(12) United States Patent
Drapeau et al.

(10) Patent No.: US 8,697,107 B2
(45) Date of Patent: Apr. 15, 2014

(54) FLOWABLE IMPLANT WITH CROSSLINKABLE SURFACE MEMBRANE

(75) Inventors: Susan J. Drapeau, Collierville, TN (US); Daniel A. Shimko, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/458,286

(22) Filed: Apr. 27, 2012

(65) Prior Publication Data

US 2013/0287817 A1    Oct. 31, 2013

(51) Int. Cl.
*A61K 47/36* (2006.01)
*A61K 38/18* (2006.01)
*A61K 38/17* (2006.01)
*A61K 38/21* (2006.01)

(52) U.S. Cl.
USPC ......... 424/422; 424/400; 424/93.1; 424/93.7; 424/93.71; 424/93.72; 424/93.73; 424/85.1; 424/85.5; 514/8.1; 514/8.2; 514/8.5; 514/8.8; 514/8.9; 514/9.1; 514/16.7; 514/769

(58) Field of Classification Search
None
See application file for complete search history.

(56) References Cited

U.S. PATENT DOCUMENTS

| | | | |
|---|---|---|---|
| 4,623,553 A * | 11/1986 | Ries et al. ................. 427/2.27 |
| 4,877,864 A | 10/1989 | Wang et al. | |
| 5,013,649 A | 5/1991 | Wang et al. | |
| 5,106,748 A | 4/1992 | Wozney et al. | |
| 5,108,922 A | 4/1992 | Wolfbeis | |
| 5,116,738 A | 5/1992 | Wang et al. | |
| 5,187,076 A | 2/1993 | Wozney et al. | |
| 5,270,300 A * | 12/1993 | Hunziker ................. 514/13.3 |
| 5,366,875 A | 11/1994 | Wozney et al. | |
| 5,676,699 A * | 10/1997 | Gogolewski et al. ...... 623/16.11 |
| 6,030,635 A | 2/2000 | Gertzman et al. | |
| 6,326,018 B1 | 12/2001 | Gertzman et al. | |
| 6,808,585 B2 * | 10/2004 | Boyce et al. ............. 156/244.11 |
| 6,911,212 B2 | 6/2005 | Gertzman et al. | |
| 7,172,629 B2 | 2/2007 | McKay | |
| 7,563,455 B2 | 7/2009 | McKay | |
| 7,671,014 B2 | 3/2010 | Beals et al. | |
| 8,101,676 B2 | 1/2012 | McKay | |
| 2008/0147197 A1* | 6/2008 | McKay ...................... 623/23.51 |
| 2008/0152691 A1* | 6/2008 | Drapeau et al. ............ 424/426 |
| 2009/0054983 A1* | 2/2009 | Wuisman et al. .......... 623/16.11 |
| 2009/0246244 A1 | 10/2009 | McKay et al. | |
| 2009/0264391 A1 | 10/2009 | King | |
| 2010/0226959 A1* | 9/2010 | Mckay ......................... 424/425 |

OTHER PUBLICATIONS

Smith, Brent, et al., Ionic Crosslinking, A Novel Method of Fabric Stabilization, NCT Project: C04-NS01, National Textile Center Research Briefs, Chemistry Compentency: Jun. 2005, 2 pages.

(Continued)

*Primary Examiner* — Tracy Vivlemore
*Assistant Examiner* — Monica Shin
(74) *Attorney, Agent, or Firm* — Sorell Lenna & Schmidt LLP

(57) ABSTRACT

A flowable biomedical implant for application to a bone defect to promote bone growth is provided. The flowable biomedical implant comprises a carrier matrix including a biodegradable polysaccharide and ceramic material. An impermeable membrane can be integrally formed at the surface of the carrier matrix by applying a crosslinking agent to the biodegradable polysaccharide mixed with ceramic materials.

20 Claims, 3 Drawing Sheets

(56) References Cited

OTHER PUBLICATIONS

Aiedeh, Khaled M., et al., Communication, Effect of Ionic Crosslinking on the Drug Release Properties of Chitosan Diacetate Matrices, Journal of Pharmaceutical Sciences, vol. 96, No. 1, Jan. 2007, 7 pages.

Pierog, Milena, et al., Effect of Ionic Crosslinking Agents on Swelling Behaviour of Chitosan Hydrogel Membranes, Progress on Chemistry and Application of Chitin and Its . . . , vol. XIV, 2009, 8 pages.

Moura, M. Jose, et al., In Situ Forming Chitosan Hydrogels Prepared via Ionic/Covalent Co-Crossing-Linking, BioMacromolecules, ACS Publications, American Chemistry Society, 2011, 12, 3275-3284.

* cited by examiner

FLOWABLE IMPLANT WITH CROSSLINKABLE SURFACE MEMBRANE

FIELD

The present disclosure generally relates to a biomedical implant and more specifically, to a flowable, osteogenic implant having a crosslinkable surface membrane.

BACKGROUND

Bone grafting has been commonly used to augment healing in the treatment of a broad range of musculoskeletal disorders. This procedure has several disadvantages. If the bone material is obtained from donors of the same species, such as an allograft, an increased risk of disease transmission and immune reaction exists. Bone material surgically removed from the patient, known as an autograft, is also undesirable because a sufficient amount of autogenous bone may not be available and the additional surgery necessary to obtain the autograft increases the risk of infection.

Both autografts and allografts have their drawbacks and therefore safer bone graft substitutes would be beneficial. These safer substitutes are usually constituted from non-bone derived materials. These safer substitutes ideally should be biocompatible, bioresorbable, osteoconductive, osteoinductive and osteogenic for the generation of new bone at the site of injury (i.e., at intended bone graft site). In addition, the implant should not be infiltrated by other surrounding soft tissue cells that may interfere with bone tissue growth. Ideally the implant should also provide an environment that is maximally conducive for new bone growth at the intended target site. Any soft tissue cells that infiltrate the porous implant surface will inhibit the process of new bone growth or even truncate the developmental pathway to new bone tissue. This type of problem may cause a severely weakened graft or even a non-union and hence a failed implant. Failed implants have increased morbidities, impose additional suffering upon patients, and increased costs for both patient and society.

Therefore, there continues to be a need for improved bone implant materials that address the issue of cellular fibrous tissue in-growth into the implant which potentially interferes with new bone growth. The present disclosure addresses this need.

SUMMARY

A flowable biomedical implant for application to a bone defect to promote bone growth is provided. The flowable biomedical implant comprises a carrier matrix including a biodegradable polysaccharide and ceramic particles. An impermeable membrane can be integrally formed at the surface of the carrier matrix by contacting the biodegradable polysaccharide including the ceramic particles with 0.1% by weight to about 20% by weight of a crosslinking agent. The resulting membrane forms a seal inhibiting soft tissue cells from growing into the bone defect that can reduce or prevent bone growth in the bone defect.

In various embodiments, the flowable biomedical implant includes an effective amount of a therapeutic agent incorporated into the carrier matrix to enhance bone growth. In various embodiments, the therapeutic agent comprises a bone morphogenetic protein or a LIM mineralization protein, or comprises a nucleotide sequence encoding a bone morphogenetic protein or a LIM mineralization protein, or osteogenic progenitor cells, autograft bone marrow, allograph bone marrow, transforming growth factor-beta, fibroblast growth factor, platelet derived growth factor, insulin-like growth factor, microglobulin-beta, antibiotics, antifungal agents, wetting agents, glycerol, steroids and non-steroidal anti-inflammatory compounds, analgesics or any combination thereof.

In certain embodiments the biodegradable polysaccharide of the carrier matrix includes sodium alginate, potassium alginate, calcium alginate, sodium hyaluronate, chitosan or mixtures thereof. The carrier matrix also includes ceramic material including beta tricalcium phosphate, biphasic calcium phosphate, magnesium phosphate, hydroxyapatite or mixtures thereof.

In some embodiments, the carrier matrix has a porosity of at least about 20%, at least about 10%, at least about 5%. In other embodiments, the carrier matrix comprises ceramic material in an amount from about 5% to about 95%, from about 10% to about 90%, from about 15% to about 85% by weight, from about 20% to about 70% by weight, or from about 30% to about 50% by weight of the biomedical implant.

In various embodiments, the crosslinking agent utilized can be sprayed at the surface of the carrier matrix and the crosslinking agent includes an ion source selected from barium, calcium, magnesium, copper, aluminum, zinc or mixtures thereof. The crosslinking agent can be present in an amount from about 0.1% to about 20% by weight, from about 0.1% to about 10%, from about 0.1% to about 5% by weight based on the total weight of the biomedical implant. The resulting impermeable membrane, in some embodiments, can have a thickness of about 0.1 mm to about 1 mm or 0.25 mm to 0.5 mm or less and a porosity of about 20 microns or about 15 microns or about 5 microns or less.

In various embodiments, the carrier matrix of the flowable biomedical implant can include a growth factor, an anti-inflammatory agent, an antibiotic, an analgesic, or any combination thereof. In some embodiments, the growth factor comprises at least one of: BMP-2, rhBMP-2, BMP-4, rhBMP-4, BMP-6, rhBMP-6, BMP-7[OP-1], rhBMP-7, BMP-12, rhBMP-12, BMP-13, rhBMP-13, GDF-5, rhGDF-5, Nell-1, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), PTH, PGE2 agonist, granulocyte-colony stimulating factor (G-CSF), vascular endothelial growth factor or (VEGF), mesenchymal stem cell (MSC) matrix metalloproteinase (MMP), or a statin.

In other embodiments, the carrier matrix of the flowable biomedical implant includes an effective amount of an anti-inflammatory agent and comprises anti-cytokine agents selected from at least one of: TNF-a inhibitors, IL-1 inhibitors, IL-6 inhibitors, IL-8 inhibitors, IL-12 inhibitors, IL-15 inhibitors, MMP inhibitors, IL-10, NF Kappa B inhibitors, Interferon-gamma (IFN-gamma) or mixtures thereof.

The present application also provides a method of forming a flowable biomedical implant for application to a bone defect to promote bone growth, the method comprising providing a carrier matrix, which comprises a polysaccharide and ceramic material; introducing the carrier matrix into the bone defect; applying a crosslinking agent to the surface of the carrier matrix present in the bone defect to form an impermeable membrane configured to inhibit soft tissue cells from growing into the bone defect, wherein the crosslinking agent is present in the carrier matrix in an amount of from about 0.1 wt. % to about 20 wt. %.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
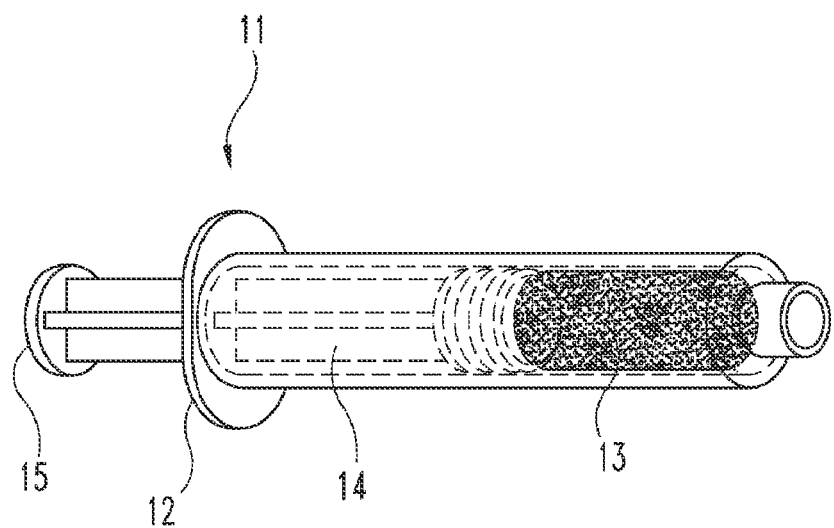
FIG. 1 illustrates a perspective view of a syringe including a carrier matrix or a therapeutic agent packaged within a terminally sterilized syringe device.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

The present disclosure may be understood more readily by reference to the following detailed description of the disclosure presented in connection with the accompanying drawing figures, which form a part of this disclosure. It is to be understood that this disclosure is not limited to the specific formulation, methods, conditions or parameters described and/or shown herein, and that the terminology used herein is for the purpose of describing particular embodiments by way of example only and is not intended to be limiting of the claimed disclosure.

As used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

As used herein, the terms "having", "containing", "including", "comprising" and the like are open ended terms that indicate the presence of stated elements or features, but do not preclude additional elements or features.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Bioactive agent or bioactive compound or therapeutic agent is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, antihistamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present application may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmacopeia Convention, Inc., Rockville Md., 2001, each of which is incorporated herein by reference.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

The term "flowable" as used herein applies to compositions whose consistencies range from those which can be described as shape-sustaining but readily deformable, e.g., those which behave like putty, to those which are runny. Specific forms of flowable implant compositions include, suspensions, solutions, gels, cakes, pastes, putty, creams, fillers or the like.

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

The term "mammal" refers to organisms from the taxonomy class "mammalian," including but not limited to humans, other primates such as chimpanzees, apes, orangutans and monkeys, rats, mice, cats, dogs, cows, horses, etc.

The term "solid" is intended to mean a rigid material, while "semi-solid" is intended to mean a material that has some degree of flexibility, thereby allowing the depot to bend and conform to the surrounding tissue requirements.

A "therapeutically effective amount" or "effective amount" is such that when administered, the drug or osteogenetic enhancing agent results in alteration of the biological activity, such as, for example, enhancing bone growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired.

The term "tissue" includes soft tissue, ligaments, tendons, cartilage and/or bone unless specifically referred to otherwise.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Flowable Biomedical Implant Formulations

As disclosed herein, in certain aspects, this disclosure relates to flowable biomedical implant formulations and to methods for making and using these implants. In various embodiments, these biomedical implants are utilized for application to a bone defect to promote bone growth and they comprise a carrier matrix including a biodegradable polysaccharide mixed with ceramic particles and a membrane integrally formed at the surface of the carrier matrix, the membrane comprising the biodegradable polysaccharide crosslinked with about 0.1 wt. % to about 20 wt. % of a crosslinking agent. In certain embodiments, the carrier matrix further comprises an effective amount of an osteogenic factor incorporated therein to cause new bone growth.

Medical grade polysaccharides suitable for use in aspects of the current application can be prepared using known techniques or purchased from commercial sources. Illustratively, purification techniques for preparing medical grade polysaccharides may include conventional separation techniques such as chromatography, membrane filtration, precipitation, extraction, or other suitable techniques. Medical grade sodium alginate may be commercially obtained, for example, from Medipol SA (Lausanne, Switzerland), or from NovaMatrix FMC Biopolymer (Philadelphia, Pa., Ultrapure PRONOVA brand (endotoxin level <100 endotoxin units per gram)).

Polysaccharides that can be used alone or in combination in the carrier matrix include, for example, alginate, hyaluronic acid, chitosan, chondroitin sulfate, dextran, dextran sulfate, heparin, heparin sulfate, gellan gum, xanthan gum, guar gum, and K-carrageenan, starch (e.g. potato starch, wheat starch, or corn starch), or mixtures of two or more of these or other polysaccharides.

Alginate polymers comprise anionic polysaccharides which include a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks) or alternating M and G-residues (MG-blocks).

Alginates contain large variations in the total content of M and G, and the relative content of sequence structures also varies largely (G-blocks, M-blocks and MG alternating sequences) as well as the length of the sequences along the polymer chain. In some embodiments, one or more alginate polymers of the flowable implant composition can contain more than 50% alpha-L-guluronic acid. In some embodiments, one or more alginate polymers of the composition can contain more than 60% alpha-L-guluronic acid. In some embodiments, one or more alginate polymers of the composition can contain 60% to 80% alpha-L-guluronic acid.

In certain embodiments, alginate polymers used in compositions as described herein may have average molecular weights ranging from 2 to 1000 kilodaltons (kD). The molecular weight of alginates can affect the properties of the flowable implant composition. Generally, lower molecular weight alginates will be more biodegradable. In some embodiments, the alginate polymers have an average molecule weight of from 5 to 350 kD. In some embodiments, the alginate polymers have an average molecule weight of from 2 to 100 kD. In other embodiments, the alginate polymers have an average molecule weight of from 50 to 500 kD. In some embodiments, the alginate polymers have an average molecule weight of from 100 to 1000 kD. The molecular weights identified in this paragraph can similarly apply to other polysaccharides when used in this disclosure.

The alginate, in some embodiments, when used, may possess a viscosity in a 1% solution measured at 20° C. of from 25 to 1000 mPas and in some embodiments, 50 to 1000 mPas (1% solution, 20° C.).

In other embodiments, the polysaccharide polymer of the carrier matrix can be chitosan. Produced commercially by deacetylation of chitin, the molecular weight of commercially produced chitosan is between 3800 and 20,000 Daltons.

Hyaluronan or hyaluronic acid, an anionic, nonsulfated glycosaminoglycan is also useful for the carrier matrix described herein. A polymer of disaccharides, each composed of D-glucuronic acid and D-N-acetylglucosamine, hyaluronan can be 25,000 disaccharides in length. Polymers of hyaluronan can range in size from 5,000 to 20,000,000 Da.

In some embodiments, the implantable membrane comprises a modulus of elasticity in the range of about $1 \times 10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

Ceramic Materials

The carrier matrix used in accordance with various embodiments of the present application includes ceramic material that is effective to provide a scaffold for bone ingrowth as the resorbable carrier and other more rapidly resorbed elements of the implant composition are resorbed. Illustratively, the ceramic material can be selected from one or more materials from the group consisting of beta-tricalcium phosphate, biphasic calcium phosphate, magnesium phosphate, hydroxyapatite, corraline hydroxyapatite, and other biocompatible ceramics.

The ceramic materials may comprise calcium compounds. For example, useful calcium compounds can comprise without limitation calcium carbonate, calcium sulfate, calcium lactobionate, calcium fluorite, calcium fluorophosphates, calcium chlorophosphate, calcium chloride, calcium lactate, hydroxyapatite, ceramics, calcium oxide, calcium monophosphate, calcium diphosphate, tricalcium phosphate, calcium silicate, calcium metasilicate, calcium silicide, calcium acetate, and biphasic calcium phosphate.

In certain embodiments, the carrier matrix described herein contains beta-tri-calcium phosphate in an amount from about 45% to about 85% weight by weight of the carrier formulation, from about 50% to about 75% weight by weight of the carrier formulation.

In various embodiments, biphasic calcium phosphate can be used as the ceramic material, with a biphasic calcium phosphate having a tricalcium phosphate:hydroxyapatite weight ratio from about 50:50 to about 95:5. In certain embodiments, the biphasic calcium phosphate contains a tricalcium phosphate:hydroxyapatite weight ratio from about 70:30 to about 95:5. In other embodiments, the biphasic calcium phosphate contains a tricalcium phosphate:hydroxyapatite weight ratio from about 80:20 to about 90:10, or to about 85:15. The ceramic material has an approximate porosity of at least 20%. Generally, the amount of mineral in the biomedical implant must be sufficient to allow for the formation of an osteoid in the bone void or target site. Further, the composition of the carrier matrix must be such that the scaffold is maintained for a sufficient amount of time for osteoid formation and eventual bone formation.

When placed in a bone void, the carrier matrix with its porous structure provides scaffolding for the migration, transformation, and attachment of new bone tissue cells. During the process of osteogenesis the carrier matrix is gradually replaced with bone tissue as the injury site is repaired.

The osteogenic implant primarily stimulates osteoblasts, which are responsible for formation of new bone tissue. Alternatively the osteogenic component may stimulate chondrocytes that may then go through endrochondral ossification to form new bone tissue. To facilitate the growth of new bone, in some embodiments, the carrier matrix comprises a high mineral content. The high mineral content primarily ensures that enough ceramic is available as new bone formation progresses at the target site and that bone generation occurs before the carrier matrix is degraded away. Further, the necessary level of mineral content required in the composition will also partially depend on the level of osteogenic activity. That is, the higher the growth factor activity level the greater the mineral content required maintaining bone formation.

In some embodiments, the ratio of ceramic mineral to bioresorbable polysaccharide is at least 3:1 by weight and in other embodiments at least 10:1. In various embodiments, the particulate mineral will constitute from about 40% to about 75% by weight of the implant. Further, in some embodiments, the mineral component has an average particle size of at least about 0.1 mm, in other embodiments from about 0.5 mm to about 2 mm, and in yet other embodiments from about 0.5 mm to about 1.5 mm.

The polysaccharide will sometimes be incorporated into flowable biomedical implant formulations at levels lower than the ceramic particles. Accordingly, in certain embodiments, the flowable implant compositions of the current application contain the polysaccharide at a level of from about 5 wt. % to about 35 wt. % on dry basis of the implant composition. In other embodiments, the flowable implant compositions contain from about 10 wt. % to about 30 wt. %, from about 15 wt. % to about 25 wt. % on dry basis of the implant composition. In other embodiments, the polysaccharide can be delivered in deionized water in amounts from about 10% to about 30% weight by volume, from about 15% to about 25% weight by volume. It will be understood that the properties of a specific alginate composition utilized will impact its effect upon the characteristics of the overall flowable implant composition, and that the amount or level of alginate in inventive compositions may vary, in certain embodiments, from those specified herein.

The biomedical implant described herein is useful in a variety of diseases, disorders, and defects where new bone formation is an essential part of the therapy. The biomedical implant is useful for long bone defects such as in the femur, tibia, fibula, and humerus and also for vertebral body defects. The implant is particularly useful in periodontal diseases where the alveolar bone requires additional new bone growth to support dental implants. Essentially the implant is especially useful where overlying soft tissues cover the target area or defect. In some embodiments, the implant is formed by preparing a putty of alginate or a similar polysaccharide and ceramic particles dry or in deionized water with or without an osteogenic enhancing agent dry or in deionized water as the hydrating agent. The resulting putty or carrier matrix is sufficiently malleable or flowable to be easily inserted into a bone defect. By spraying a crosslinking agent onto the surface of this carrier matrix a solid impermeable membrane is almost instantly formed on the surface of the carrier matrix. The impermeable solid membrane formed in this manner prevents interfering soft tissue infiltration into the biomedical implant and facilitates new bone formation. In some embodiments, the resulting putty is non-settleable, however, in certain other embodiments, once placed in the bone defect that putty can harden.

Membrane

The integrally formed membrane onto the surface of the carrier matrix provides a solid or semi-solid impermeable barrier, which resists the passage of soft tissue cells that may potentially migrate into the porous carrier matrix. Soft tissue cells, such as muscle cells, connective tissue, fibroblasts, or mast cells can infiltrate the porous carrier matrix. Further, an inflammatory response may be present at the site of injury or implant site and additional cell types and cellular components, including but not limited to neutrophils, monocytes, lymphocytes, eosinophils, basophils, and proteoglycans could infiltrate the implant post-surgically. The portion of the implant exposed to the soft tissue will have a solid impermeable membrane integrally incorporated into the biomedical implant to prevent the movement of cells and cellular components into the porous areas of the implant and thus facilitate osteogenesis at the intended target site. In this way, the impermeable membrane inhibits soft tissue infiltration into the bone defect and allows bone cells to remain unimpeded and influx the surface adjacent to or contacting the bone defect to grow bone.

As described above, the membrane barrier can be formed by spraying or contacting the surface of the carrier matrix including degradable polysaccharides such as, alginate, chitosan and hyaluronic acid and ceramic particles with a crosslinking agent such as, for example, calcium, magnesium, zinc, iron, or strontium and chlorides, gluconates, fluorides, citrates, phosphates, tartrates, sulphates, acetates, borates thereof. The cross-linking agent can be in liquid (e.g., suspension or solution) or powdered form.

The cross-linking agent can contact the carrier matrix by spraying, dripping, brushing, coating or the like the surface of the carrier matrix that surrounds the bone defect. After the crosslinking agent contacts the carrier matrix, the portion that is contacted with it forms a membrane of cross-linked matrix. In some embodiments, the membrane can form within 10 seconds to about 10 minutes.

In certain embodiments, the addition of monovalent, divalent or other polyvalent ionic species to the flowable polysaccharide ceramic matrix serves to form the impermeable solid or semi-solid membrane on the surface of the carrier matrix, which reduces soft tissue cells from growing into the bone defect. Aqueous solutions of ionic polysaccharides can generally form ionically-crosslinked gels upon contact with aqueous solutions of counter-ions. For instance, useful agents for ionically crosslinking alginate, chitosan, pectin and other similar polysaccharides to form the impermeable, solid or semi-solid surface membrane for the carrier matrix include cationic gelling agents, such as for example, divalent or trivalent cations. Useful divalent cations for this purpose include the alkaline earth metals, especially calcium, magnesium, zinc or strontium. Aluminum is a useful crosslinking trivalent cation. These ionic crosslinking agents will usually be provided in salt form. Useful anionic counter-ions for the calcium or other salts are desirably selected from pharmaceutically acceptable anions such as chlorides, gluconates, fluorides, citrates, phosphates, tartrates, sulphates, acetates, borates, or the like.

In certain embodiments, calcium chloride is the ionic crosslinking agent utilized with an alginate or pectin compound to form the impermeable, solid membrane on the surface of the flowable carrier matrix. The ionic polysaccharide chitosan can also be used, and can be ionically crosslinked with multivalent, anionic gelling agents. Such agents include metal polyphosphates, such as an alkali metal or ammonium polyphosphate, pyrophosphates or metaphosphates. Citrates can also be used. These anionic crosslinking agents will also usually be provided in salt form. The cationic counter-ion for the polyphosphate or other salt can be any suitable, biocompatible or pharmaceutically-acceptable cation including for instance sodium, potassium, or ammonium. Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides, which gel in the presence of monovalent cations, such as gellan gums, can also be used. Such polysaccharides may form gels upon exposure, for example, to a solution comprising physiological levels of sodium. Many other biocompatible polysaccharides, including plant-derived and animal-derived materials, as well as corresponding ionic crosslinking agents, are known and can also be used in certain other embodiments.

Thus, within aspects of the present disclosure, in some embodiments, a relatively small amount of crosslinking agent is added to the surface of the carrier matrix in order to form the impermeable solid or semi-solid membrane on the surface of the carrier matrix. In various embodiments, the flowable compositions as described herein can be contacted with an amount of a liquid medium containing an ionic crosslinking agent immediately prior to, during, or after implantation of the carrier matrix into a patient. Illustratively, the content of a syringe containing a mixture of sodium alginate and β-tricalcium phosphate either dry or in deionized water can be admixed with the content of another syringe containing an osteoconductive or bioactive agent either dry or in deionized water as the hydrating fluid either as part of single syringes or a dual barrel syringe system to form the flowable carrier matrix described herein as a filler for bone defects. Subsequently, a small amount of crosslinking agent, for example $CaCl_2$, in an amount from about 0.5% to about 2.5%, from about 0.5% to about 1.5% from a third syringe can be sprayed or otherwise applied to the carrier matrix surface over a relatively short period of time, for example 10 seconds to form in situ the impermeable, solid or semi-solid membrane on the surface of the carrier matrix already implanted into the bone defect. The impermeable solid or semi-solid membrane formed in this manner can have a thickness of about 1 mm or less and a porosity of about 20 microns or less thereby preventing fast growing soft tissue cells from penetrating the membrane to grow in the bone defect. In some embodiments, the membrane comprises a thickness of 0.2 mm to 1 mm and the membrane comprises pores of between about 5 microns to about 20 microns.

In some embodiments, the membrane comprises a plurality of pores. In some embodiments, at least 10% of the pores are between about 5 micrometers and about 20 micrometers at their widest points. In some embodiments, at least 20% of the pores are between about 5 micrometers and about 20 micrometers at their widest points. In some embodiments, at least 30% of the pores are between about 10 micrometers and about 20 micrometers at their widest points. In some embodiments, at least 50% of the pores are between about 10 micrometers and about 20 micrometers at their widest points. In some embodiments, at least 90% of the pores are between about 15 micrometers and about 20 micrometers at their widest points. In some embodiments, at least 95% of the pores are between about 5 micrometers and about 20 micrometers at their widest points. In some embodiments, 100% of the pores are between about 5 micrometers and about 20 micrometers at their widest points. The pore may support ingrowth of bone cells, and/or formation or remodeling of bone.

In some embodiments, a method of forming a flowable biomedical implant for application to a bone defect to promote bone growth is provided, the method comprising providing a carrier matrix, which comprises a polysaccharide and ceramic material. The carrier can be contacted with a crosslinking agent (for example and ionic and covalent crosslinking agent). If the pH of the crosslinking agent is too high or too low, the cross linking agent can be neutralized using a neutralizing agent with crosslinking properties (e.g., ionic crosslinking agent). This crosslinking of the membrane forms an impermeable barrier configured to inhibit soft tissue cells from growing into the bone defect, wherein the crosslinking agent is present in the carrier matrix in an amount of from about 0.1 wt. % to about 20 wt. %.

In some embodiments, the flowable biomedical implant cross-linking agent couples to the carrier matrix by ionic and covalent cross-linking Genipin can be used as a chemical cross-linker in an amount of about 0.05, about 0.10, about 0.15, about 0.20% w/w for chitosan hydrogels. This can then be neutralized with a neutralizing agent, such as for example, glycerol, which can be in a glycerol-phosphate complex form, particularly when forming impermeable membranes on chitosan hydrogels. This will enhance the crosslinking performance of the matrix to form an impermeable membrane.

In some embodiments, cellulose can be crosslinked by reacting cellulose with chloroacetic acid (CAA) to attach negative anionic sites to cellulose fibers of the matrix, then treating the anionic cellulose with polycations such as, for example, cationized chitosan (C Chitosan), cationized glycerine (C Glycerin), cationized ethylene glycol, cationized dextrose and cationized D-Cellobiose to attain improved dry wrinkle recovery performance. The wrinkle recovery performance can be improved by the addition of divalent cations such as, for example, Ca++ and Mg++. In some embodiments, reacting cellulosic fabric with 3-chloro-2-hydroxypropyl trimethyl ammonium chloride (CHTAC) to attach positive cationic sites to the fiber, then treating the fiber with a variety of polyanions such as, for example, polymaleic acid (PMA), 1,2,3,4-butanetetracarboxylic acid (BTCA), ethylenediaminetetraacetic acid, nittrilo-triacetic acid, di o-hydroxyphenylacetic acid, oxalic acid, citric acid and malic acid. This will enhance crosslinking.

In some embodiments, the carrier matrix can be cross-linked with $Al^{3+}$, $Zn^{2+}$ and $Ca^{2+}$ ions to yield ionotropically cross-linked polymeric matrices. In some embodiments, chitosan can be physically cross-linked by treating the chitosan with sulfuric acid, trisodium citrate, sodium tripolyphosphate, and sodium alginate. These are just some of the ways to crosslink the polysaccharide to form the impermeable membrane barrier.

In some embodiments, the membrane has at least 10% of the pores between about 50 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 50 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 50 micrometers and about 300 micrometers at their widest points.

In some embodiments, the matrix portion that does not contain the membrane can comprises a plurality of pores. In some embodiments, at least 10% of the pores are between about 50 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 50 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 50 micrometers and about 300 micrometers at their widest points.

In some embodiments, the matrix portion that does not contain the membrane has a porosity of at least about 30%, at least about 50%, at least about 60%, at least about 70%, at least about 90%. The pore may support ingrowth of cells, formation or remodeling of bone, cartilage and/or vascular tissue.

Compositions of the present application can be manufactured in a ready-to-use format and packaged in a medically acceptable container for dry or wetted flowable materials. In some embodiments, as illustrated in FIG. 1, the ready-to-use carrier matrix component can be a product 11 including a syringe device 12 containing either an amount of biodegradable polysaccharide containing ceramic particles or osteogenic enhancing agent 13 of the current application. Either the carrier matrix or the bioactive agent (e.g., osteogenic enhancing agent) can be contained within syringe barrel 14, and is transferable from the barrel 14 by actuating a plunger 15.

Figure 2:
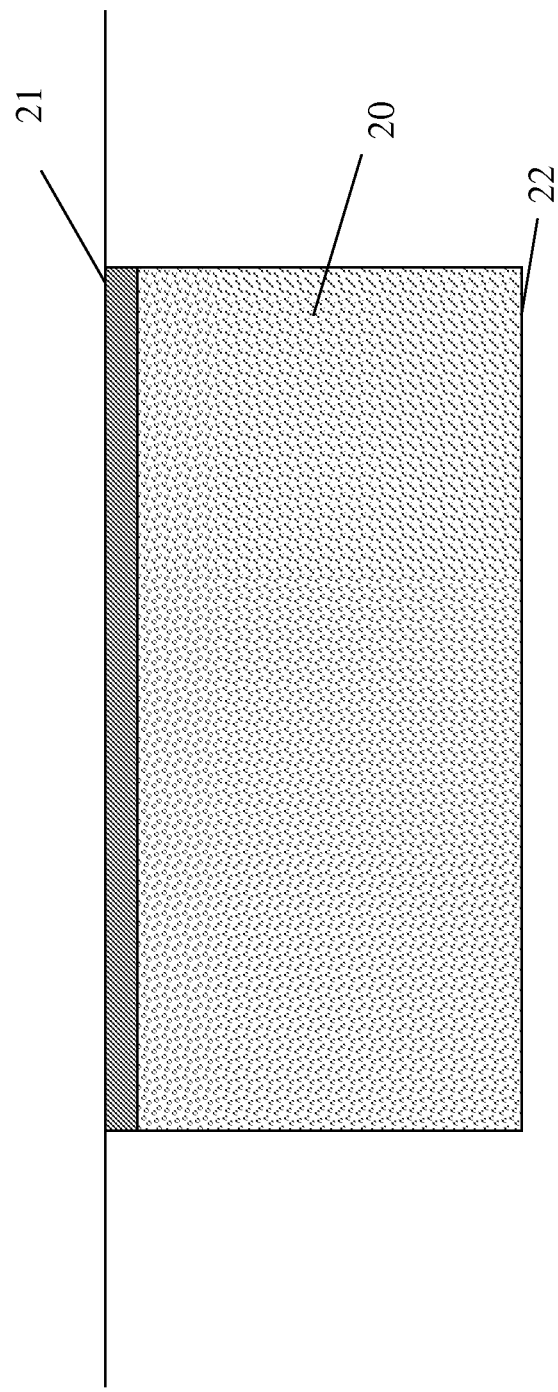
FIG. 2 is a cross-sectional diagrammatical view of the implant indicating the bone void filler with a solid membrane integrally formed at the surface.

A side or cross-sectional view as illustrated in FIG. 2 shows the porous bone void filler 20 and the solid or semi-solid impermeable membrane 21 that has the particular thickness and low porosity discussed above that will reduce influx of non-bone cells like soft tissue cells (e.g., muscle cells, vascular cells, cartilage cells, etc.) from competing with bone cells (osteoblasts, osteoclasts, etc.) entering the matrix and/or the bone defect 22. In this way, the matrix contacts bone and bone cells will enter it unimpeded by the faster growing soft tissue cells and therefore the bone defect will be remodeled and repair at a faster rate.

Bioactive Agents

In some embodiments, the compositions comprise a bioactive agent including an osteoinductive factor, such as an osteoinductive protein or a nucleotide sequence encoding an osteoinductive protein operably associated with a promoter (e.g., provided in a vector such as a viral vector) which drives expression of the gene in the animal recipient to produce an effective amount of the protein. As discussed above, the osteogenic factor utilized in the present application can be one that stimulates production or activity of the osteoblasts. The factor can be a bone morphogenetic protein (BMP) or a LIM mineralization protein (LMP), or comprises a nucleotide sequence encoding a BMP or LMP or any combination thereof. Recombinant human BMPs may be commercially obtained or prepared as described and known in the art, e.g. in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; and WO94/26892 to Celeste et al. Further, the osteoinductive factor may be isolated from bone. Methods for isolating BMP from bone are described in U.S. Pat. No. 4,294,753 to Urist and Urist et al., PNAS 371, 1984. Recombinant human BMP-2 (rhBMP-2), recombinant human BMP-4 (rhBMP-4), BMP-6, rhBMP-6, BMP-7[OP-1] recombinant human BMP-7 (rhBMP-7), Nell-1, recombinant human growth differentiation factor (rhGDF-5), statins, or heterodimers thereof are more preferred. However, in some embodiments, the growth factor that can be used comprises rhBMP-2, rhBMP-7, rhGDF-5 or a combination thereof. The osteoinductive factor may also be LMP or a suitable vector incorporating a gene encoding the same operably associated with a promotor, as described in WO99/06563 (see also genbank accession No. AF095585). When such vectors are employed as osteogenic factors in accordance with the invention, they are preferably delivered in conjunction with cells, for example autologous cells from the recipient of the implant. Most preferably the vector is delivered in conjunction with autologous white blood cells derived from bone marrow or peripheral blood of the recipient. These cells may be applied to the sponge composition along with the osteogenic factor prior to implantation.

Further, as an example, BMP or other osteogenic enhancing agents may be included in the carrier matrix by combining the BMP with a liquid carrier as known in the art and combining with the carrier matrix as described in the examples below.

In some embodiments, other growth factors or osteogenic enhancing agents may be incorporated into the composition. Such additional agents include host compatible osteogenic progenitor cells, autographic bone marrow, allographic bone marrow, transforming growth factor-beta (TGF-beta), fibroblast growth factor (FGF), platelet-derived growth factor (PDGF), insulin-related growth factor (IGF-I), insulin-related growth factor-II (IGF-II) beta-2-microglobulin (BDGF II), PTH, PGE2 agonist, granulocyte-colony stimulating factor (G-CSF), vascular endothelial growth factor (VEGF), mesenchymal stem cells (MSC), matrix metalloproteinase (MMP), peptides, a statin, antibiotics and steroids.

Additional enhancements may comprise an effective amount of anti-inflammatory agents, such as anti-cytokine agents. Anti-cytokine agents may comprise TNF-a inhibitors, IL-1 inhibitors, IL-6 inhibitors, IL-8 inhibitors, IL-12 inhibitors, IL-15 inhibitors, IL-10, NF Kappa B inhibitors, and interferon-gamma (IFN-gamma).

Still further enhancements may include effective amounts of antibiotics and analgesics. These agents are well known in the art. In different embodiments of the invention, other active ingredients may also be added to the carrier matrix. An active ingredient may include an antimicrobial, antifungal, antiviral, an antineoplastic agent, an antibiotic, an analgesic, narcotic antagonists, and any combination thereof, in addition to one or more anti-cytokine agents.

A suitable agent may include an analgesic such as morphine, a suitable narcotic antagonist (e.g., naloxone), local anaesthetics (e.g., lidocaine, bupivacaine, mepivacaine, dibucaine, prilocalne, etidocaine, ropivacaine, procaine, tetracaine, etc.), glutamate receptor antagonists, adrenoreceptor agonists, adenosine, canabinoids, cholinergic and GABA receptors agonists, and different neuropeptides. A detailed discussion of different analgesics is provided in Sawynok et al., (2003) Pharmacological Reviews, 55:1-20, the contents of which are incorporated herein by reference.

Suitable antibiotics include, without limitation nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol and any combination thereof.

Kits

The present invention also provides medical kits that include, or that can be used to prepare the flowable biomedical implant compositions of the invention. Such kits can include a dried material containing the solid ingredients of the flowable biomedical implant formulation along with an aqueous medium or other biocompatible wetting liquid with or without the osteogenic enhancing factor for combination with the dried material to form a flowable wetted material, or can include the formulated, wetted flowable implant material in a suitable container such as a syringe or vial (e.g. terminally sterilized), and/or a transfer device such as a syringe, and/or a therapeutic substance, for example an osteogenic substance such as a growth factor. In one specific form, such a medical kit can include a dried material, such as a particulate or dried body, a growth in lyophilized form (e.g. rhGDF-5), and an aqueous medium for reconstitution of the growth factor to prepare an aqueous formulation that can then be added to the dried material in the process of preparing an osteogenic putty, paste or other flowable implant material of the invention.

In various embodiments, a kit is provided that may include additional parts along with the drug depot and/or medical device combined together to be used to implant the drug depot. In another embodiment, the kit may include a device such as a syringe or vial including the biodegradable polysaccharide admixed with ceramic particles in a first compartment. The second compartment may include another device such as a syringe or vial holding dry osteogenic enhancing agent as a dry powder or in deionized water for combining with the contents of the first syringe. A third compartment may include a third syringe including the crosslinking agent for spraying the carrier matrix to form a surface membrane integrally formed with the biomedical implant. A fourth compartment may include gloves, drapes, wound dressings and other procedural supplies for maintaining sterility of the implanting process, as well as an instruction booklet. A fifth compartment may include additional syringes and/or needles. A six compartment may comprise an agent for radiographic imaging. Each tool may be separately packaged in a plastic pouch that is radiation sterilized. A cover of the kit may include illustrations of the implanting procedure and a clear plastic cover may be placed over the compartments to maintain sterility.

Sterilization

The carrier matrix and/or each medical device utilized to prepare the carrier matrix, for example syringes or vials, can be sterilizable. In various embodiments, one or more components of the carrier matrix, and/or medical device to administer the carrier matrix and/or osteogenic enhancing agent are sterilized by radiation in a terminal sterilization step in the final packaging. Terminal sterilization of a product provides greater assurance of sterility than from processes such as an aseptic process, which require individual product components to be sterilized separately and the final package assembled in a sterile environment, although aseptic manufacturing is also useful for the flowable biomedical implants described herein.

Typically, in various embodiments, gamma radiation is used in the terminal sterilization step, which involves utilizing ionizing energy from gamma rays that penetrates deeply in the device. Gamma rays are highly effective in killing microorganisms. They leave no residues and do not have sufficient energy to impart radioactivity to the device.

Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the carrier matrix and/or one or more components of the delivery devices, including, but not limited to, gas sterilization, such as, for example, with ethylene oxide or steam sterilization.

The invention can best be understood by the following examples with the percentages being determined by weight or by volume. All examples could also be done in an aseptic environment to maintain a sterile final product. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

EXAMPLES

Example 1

Preparation of Sham Calvarial Bone Defects for Standard Rat Model

Full thickness flaps incisions were made to expose the parietal bone of the brain underneath. A motorized burr was used to create bilateral full-thickness 5 mm diameter bony defects. A 0.02 cc biomedical implant containing alginate/ceramic with or without a bioactive agent (e.g., GDF-5) was placed into the bony defects. Subsequently, the surgical wound associated with the sham calvarial bone defects were closed in two layers in accordance with standard surgical techniques. Animals participating in this study survived for 8 weeks and their skull recovered as a whole. Histology evaluations were conducted in order to determine new bone formation.

Preparation of Flowable Implant Formulation

Two syringes, one containing the carrier matrix and the other containing an osteogenic enhancing agent, were prepared as follows:

Syringe 1 contained 25% dry weight by weight of ultra pure medium viscosity grade (MVG) sodium alginate and 75% dry weight by weight beta-tricalcium phosphate. In another experimental run, syringe 1 contained 19% weight by volume ultra pure MVG sodium alginate and 58% weight by volume beta-tricalcium phosphate, all in deionized water. Syringe 2 contained deionized water containing no protein or with a suspended protein, such as, for example growth factor rhGDF-5.

Syringes 1 and 2 were both added to the bone defect described above in a ratio of syringe 1:syringe 2 of 3:1. Specifically, for every 0.75 cc of syringe 1, 0.25 cc of syringe 2 were added to obtain a final volume of 1 ml of final material. The final product deposited in the bone defect contained 14% weight by volume ultra pure MVG sodium alginate and 43% weight by volume beta-tricalcium phosphate. The final product samples contained rhGDF-5 growth factor in concentrations of 0 mg/cc, 0.35 mg/cc, 0.7 mg/cc or 1.5 mg/cc. After the flowable biomedical implants were filled into bone defects, a solution of 1% $CaCl_2$ was applied over a 10 second interval to form a crosslinked semi-solid membrane. The crossliked membrane provided a seal to prevent soft tissue cells from growing into the bone defect.

In this study, the osteoinductive putty materials prepared by combining syringes 1 and 2 were evaluated for their ability to form new bone in the bone defect filled with these materials. The results are shown in Table 1.

TABLE 1

| Carrier Matrix | Growth Factor | Cross linked Membrane | Results |
|---|---|---|---|
| Sham | N/A | N/S | Minimal bone formation from edges. |
| Alginate/Ceramic | None | No | Minimal bone formation. |
| Alginate/Ceramic | None | Yes | Minimal bone formation with slight inflammatory response adjacent cross-linked skin |
| Alginate/Ceramic | 0.7 mg/cc | No | Robust bone formation |
| Alginate/Ceramic | 1.5 mg/cc | No | Robust bone formation |
| Alginate/Ceramic | 0.7 mg/cc | Yes | Robust bone formation with slight inflammatory response adjacent cross-linked skin |
| Alginate/Ceramic | 1.5 mg/cc | Yes | Robust bone formation with slight inflammatory response adjacent cross-linked skin |

Sham defects showed new bone formation stemming from the intact bony borders of the defect. Bridging bone was not observed in sham operated groups. Alginate/ceramic carrier groups both with and without cross-linked semi-solid membrane showed evidence of bone formation stemming from the intact bony borders and some central bony islands were observed. Slight inflammation was noted adjacent the cross-linked semi-solid membranes in these groups, however, this had no apparent effect on bone healing within the defect. Alginate/ceramic carrier groups combined with rhGDF-5 protein showed robust bone formation at the defect site. Slight inflammation was noted adjacent the cross-linked semi-solid membranes in these groups containing rhGDF-5 as well, however, this had no apparent effect on bone healing within the defect.

Figure 3:
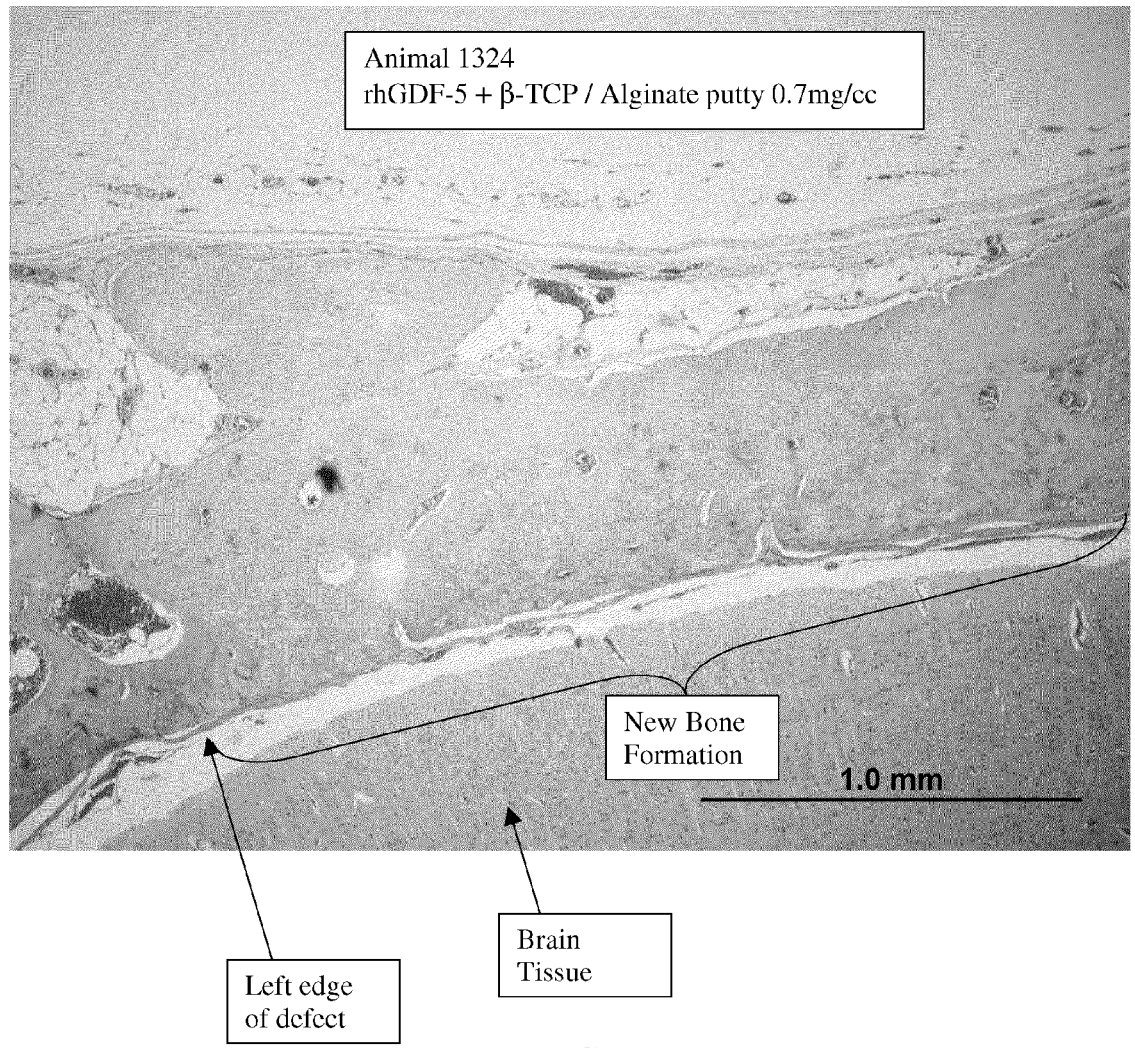
FIG. 3 is a microscopic slide illustrating a histology evaluation of the bone formation in the standard rat calvarial defect that was filled with a putty comprising and alginate/β-TCP (tri-calcium phosphate) carrier matrix, 0.7 mg/cc of rhGDF-5 and including a crosslinked membrane formed by the addition of 1% $CaCl_2$ solution.

FIG. 3 is a microscopic slide illustrating a histology evaluation of the bone formation in the standard rat calvarial defect of animal 1324 filled with a putty containing and alginate/ceramic carrier matrix, 0.7 mg/cc of rhGDF-5 and crosslinking membrane formed by the addition of 1% $CaCl_2$ solution. In FIG. 3, 50 illustrates new bone formation growing along 52, the brain tissue present in the bone defect formed in the brain of rat 1324 and 54 shows the left edge of such bone defect. It is readily apparent that the new bone growth in the defect site was robust and contained, and was not affected by soft tissue in-growth originating from the overlying periosteum.

Example 2

Preparation of Defects in Standard Rat Model to Test Intramuscular Osteoinductivity One centimeter incisions were made into caudal stifle joints of the rats used in this study. A sharp and blunt dissection was used to create a pocket between the semimembranosus and semitendinosis muscle groups. 0.2 cc implants were placed into the pockets thus created. The surgical wounds were closed in two layers in accordance with standard surgical techniques. The foregoing procedure was performed bilaterally. The animals used in this example survived for 4 weeks and implants were recovered as a whole. Histology evaluations were conducted to determine new bone formation using Osteoinductivity (OI) semi-quantitative scoring. An OI score of 0 indicates no bone formation; an OI score of 1 indicates 1%-25% bone formation; an OI score of 2 indicates 26%-50% bone formation; an OI score of 3 indicates 51%-75% bone formation; and an OI score of 4 indicates 76%-100% bone formation.

Syringes 1 and 2 were prepared in the same manner as in Example 1. Once the putty was placed into the incisions made into the caudal stifle joints, a 1% solution of $CaCl_2$ was applied over a 10 second interval to form a crosslinked semi-solid membrane. The results are shown in Table 2.

TABLE 2

| Carrier Matrix | Growth Factor | Cross linked Membrane | OI Score (OI; implants with positive score) |
|---|---|---|---|
| Alginate/Ceramic | None | No | 0; 5 of 5 |
| Alginate/Ceramic | None | Yes | 0; 5 of 5 |
| Alginate/Ceramic | 0.35 mg/cc | No | 0; 4 of 4 |
| Alginate/Ceramic | 0.7 mg/cc | No | 1; 1 of 5 |
| Alginate/Ceramic | 1.5 mg/cc | No | 1; 2 of 4 |
| Alginate/Ceramic | 0.35 mg/cc | Yes | 0; 4 of 4 |
| Alginate/Ceramic | 0.7 mg/cc | Yes | 1; 1 of 4 |
| Alginate/Ceramic | 1.5 mg/cc | Yes | 1; 3 of 4 |

The experimental results summarized in Table 2 indicate that the carrier matrix alone was not bone inductive. Addition of growth factor rhGDF-5 increased the inductive response in a step wise fashion with the highest OI score for the highest growth factor concentration of 1.5 mg/cc. When utilized in caudal stifle joints the crosslinked membrane had no effect on bone-inductive capacity of the graft.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A flowable biomedical implant for application to a bone defect to promote bone growth, the flowable biomedical implant having an essential absence of collagen, the flowable biomedical implant comprising a carrier matrix, which comprises a biodegradable polysaccharide comprising sodium alginate and ceramic material disposed within the carrier matrix, the flowable biomedical implant having a cross-linked membrane formed at a surface of the carrier matrix by a cross-linking agent, the cross-linked membrane defining an uppermost outer surface of the implant and the cross-linked membrane also comprises the sodium alginate and the ceramic material, the cross-linking agent comprising from about 0.1 wt. % to about 20 wt. % of the carrier matrix, wherein a portion of the carrier matrix that does not contain the cross-linked membrane has a porosity of at least about 50%.

2. A flowable biomedical implant according to claim 1, wherein the carrier matrix comprises about 1 wt % by weight of a crosslinking agent and the flowable biomedical implant comprises a paste or putty.

3. A flowable biomedical implant according to claim 1, further comprising a bioactive agent incorporated into the carrier matrix to enhance bone growth.

4. A flowable biomedical implant according to claim 3, wherein the bioactive agent comprises a bone morphogenetic protein, a LIM mineralization protein, a nucleotide sequence encoding a bone morphogenetic protein or a LIM mineralization protein, or osteogenic progenitor cells, autograph bone marrow, allograph bone marrow, transforming growth factor-beta, fibroblast growth factor, platelet derived growth factor, insulin-like growth factor, microglobulin-beta, antibiotics, antifungal agents, wetting agents, glycerol, steroids or non-steroidal anti-inflammatory compounds, analgesics, or any combination thereof.

5. A flowable biomedical implant according to claim 1, wherein the cross-linked membrane is a solid or semi-solid membrane that forms a seal, preventing soft tissue cells from growing into the bone defect and the membrane comprises a thickness of 0.2 mm to 1 mm and the membrane comprises pores of between about 5 microns to about 20 microns or about 50 micrometers to about 500 micrometers.

6. A flowable biomedical implant according to claim 1, wherein the ceramic material comprises beta tricalcium phosphate, biphasic calcium phosphate, magnesium phosphate, hydroxyapatite or mixtures thereof.

7. A flowable biomedical implant according to claim 1, wherein the ceramic material has a porosity of at least about 20% and the matrix comprises demineralized bone matrix.

8. A flowable biomedical implant according to claim 1, wherein the carrier matrix comprises ceramic material in an amount from about 10% to about 90%, or from about 15% to about 85% by weight of the biomedical implant.

9. A flowable biomedical implant according to claim 1 wherein the crosslinking agent comprises barium, calcium, magnesium, copper, aluminum, zinc or mixtures thereof.

10. A flowable biomedical implant according to claim 1, wherein the cross-linked membrane is a solid or semi-solid membrane that has a thickness of about 1 mm or less, and the cross-linked membrane having pores of about 20 microns or less.

11. A flowable biomedical implant according to claim 3, wherein the bioactive agent comprises BMP-2, rhBMP-2, BMP-4, rhBMP-4, BMP-6, rhBMP-6, BMP-7[OP-1], rhBMP-7, BMP-12, rhBMP-12, BMP-13, rhBMP-13, GDF-5, rhGDF-5, Nell-1, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), PTH, PGE2 agonist, granulocyte-colony stimulating factor (G-CSF), vascular endothelial growth factor or (VEGF), mesenchymal stem cell (MSC) matrix metalloproteinase (MMP), or a statin.

12. A method of forming a flowable biomedical implant for application to a bone defect to promote bone growth, the method comprising
providing a carrier matrix, which comprises a polysaccharide and ceramic material;
introducing the carrier matrix into the bone defect; and
introducing a crosslinking agent to the surface of the carrier matrix present in the bone defect to form an impermeable membrane also comprising the polysaccharide and the ceramic material and defining an uppermost outer surface of the implant, the impermeable membrane being configured to inhibit soft tissue cells from growing into the bone defect, wherein the crosslinking agent is present in the carrier matrix in an amount of from about 0.1 wt. % to about 20 wt. %, wherein a portion of the carrier matrix that does not contain the impermeable membrane has a porosity of at least about 50% and the implant has an essential absence of collagen.

13. A method according to claim 12, further comprising adding a therapeutic agent to the carrier matrix prior to introducing the carrier matrix into the bone defect.

14. A method according to claim 13, wherein the therapeutic agent comprises a bone morphogenetic protein or a LIM mineralization protein, a nucleotide sequence encoding a bone morphogenetic protein or a LIM mineralization protein, osteogenic progenitor cells, autographic bone marrow, allographic bone marrow, transforming growth factor-beta, fibroblast growth factor, platelet derived growth factor, insulin-like growth factor, microglobulin-beta, antibiotics, antifungal agents, wetting agents, glycerol, steroids and non-steroidal anti-inflammatory compounds, or any combination thereof.

15. A method according to claim 12, wherein the polysaccharide is biodegradable and comprises sodium alginate, potassium alginate, calcium alginate, sodium hyaluronate, chitosan or mixtures thereof.

16. A method according to claim 12, wherein the crosslinking agent comprises an ion source of barium, calcium, magnesium, copper, aluminum, zinc or mixtures thereof.

17. A method according to claim 12, wherein the membrane comprises a thickness of 0.2 mm to 1 mm and the membrane comprises pores of between about 5 microns to about 20 microns or about 50 micrometers to about 500 micrometers, where the crosslinking agent is present in an amount from about 0.5 wt. % to about 15 wt. % based on the weight of the biomedical implant.

18. A method according to claim 12, wherein the ceramic material comprises beta tricalcium phosphate, biphasic calcium phosphate, magnesium phosphate, hydroxyapatite or mixtures thereof.

19. A method according to claim 12, wherein the impermeable membrane is formed within 10 seconds to about 10 minutes after applying the crosslinking agent.

20. A flowable biomedical implant for application to a bone defect to promote bone growth, the implant having an essential absence of collagen, the implant comprising a carrier matrix comprising a biodegradable polysaccharide, ceramic material and bone morphogenetic protein disposed within the carrier matrix, the biodegradable polysaccharide comprising sodium alginate, the ceramic material comprising from about 10% to about 90% by weight of the implant, the implant having a cross-linked membrane comprising a cross-linking agent, the ceramic material and the polysaccharide and the cross-linked membrane defining an uppermost outer surface of the implant, wherein the membrane has a modulus of elasticity in the range of about $1\times10^2$ to about $6\times10^5$ dynes/$cm^2$, wherein a portion of the carrier matrix that does not contain the cross-linked membrane has a porosity of at least about 50%.

* * * * *